(12) United States Patent
Zougari

(10) Patent No.: US 10,610,633 B2
(45) Date of Patent: Apr. 7, 2020

(54) CONTACTLESS ACTUATION FOR VALVE IMPLANT

(71) Applicant: Mohammed Ibn khayat Zougari, LaSalle (CA)

(72) Inventor: Mohammed Ibn khayat Zougari, LaSalle (CA)

( * ) Notice: Subject to any disclaimer, the term of this patent is extended or adjusted under 35 U.S.C. 154(b) by 0 days.

(21) Appl. No.: 15/878,385

(22) Filed: Jan. 23, 2018

(65) Prior Publication Data

US 2018/0207346 A1 Jul. 26, 2018

Related U.S. Application Data

(60) Provisional application No. 62/453,476, filed on Feb. 1, 2017, provisional application No. 62/449,639, filed on Jan. 24, 2017, provisional application No. 62/449,555, filed on Jan. 23, 2017.

(51) Int. Cl.

| | |
|---|---|
| *A61M 1/36* | (2006.01) |
| *H01F 7/02* | (2006.01) |
| *A61M 39/22* | (2006.01) |
| *H01F 7/06* | (2006.01) |

(52) U.S. Cl.
CPC ........ *A61M 1/3655* (2013.01); *A61M 39/227* (2013.01); *H01F 7/02* (2013.01); *H01F 7/0242* (2013.01); *H01F 7/06* (2013.01); *A61M 2039/226* (2013.01); *A61M 2205/0288* (2013.01)

(58) Field of Classification Search
CPC .............. A61M 1/3655; A61M 39/227; A61M 2039/226; A61M 2205/0288; H01F 7/02; H01F 7/0242; H01F 7/06
See application file for complete search history.

(56) References Cited

U.S. PATENT DOCUMENTS

| | | | |
|---|---|---|---|
| 2011/0130702 A1* | 6/2011 | Stergiopulos | .......... A61B 17/12 604/9 |
| 2015/0305746 A1* | 10/2015 | Johnson | ........... A61B 17/12045 606/153 |

* cited by examiner

*Primary Examiner* — Philip R Wiest
(74) *Attorney, Agent, or Firm* — Carlson, Gaskey & Olds, P.C.

(57) ABSTRACT

An example magnetically activated implantable valve according to the present disclosure includes an implantable valve, the implantable valve including a first set of passive magnets, and an actuator configured to actuate the implantable valve. The actuator includes a second set of passive magnets corresponding to the first set of passive magnets. The first set of passive magnets is configured to interact with the second set of passive magnets to actuate the valve. Another example magnetically activated implantable valve and an implantable valve for controlling flow of an active fluid are also disclosed.

12 Claims, 14 Drawing Sheets

CONTACTLESS ACTUATION FOR VALVE IMPLANT

CROSS-REFERENCE TO RELATED APPLICATIONS

This application claims priority to U.S. Provisional Patent Application Ser. No. 62/449,555 filed Jan. 23, 2017, U.S. Provisional Patent Application Ser. No. 62/449,639 filed Jan. 24, 2017, and U.S. Provisional Patent Application Ser. No. 62/453,476 filed Feb. 1, 2017.

BACKGROUND

Some medical procedures, require implanted devices. Hemodialysis, for instance, requires vascular access (that is, access to a patient's vascular system, including veins and arteries). In some cases, vascular access is required over long periods of time and for repeat medical procedures. In such instances, an implant or graft can be placed in the patient to allow for vascular access. One example implant is an arteriovenous (AV) graft, which is a biocompatible tube that links a patient's artery and vein. The tube has access points for access from outside of the patient's body. However, the AV graft is constantly open, and thus constantly and unnaturally diverts blood flow between the patient's artery and vein and vice versa, which can cause complications.

SUMMARY

An example magnetically activated implantable valve according to the present disclosure includes an implantable valve, the implantable valve including a first set of passive magnets, and an actuator configured to actuate the implantable valve. The actuator includes a second set of passive magnets corresponding to the first set of passive magnets. The first set of passive magnets is configured to interact with the second set of passive magnets to actuate the valve.

An example magnetically activated implantable valve according to the present disclosure includes an implantable valve, the implantable valve including a set of passive magnets, and an actuator configured to actuate the implantable valve. The actuator includes a set of active magnets corresponding to the set of passive magnets, wherein the set of passive magnets is configured to interact with the set of active magnets to actuate the implantable valve.

An implantable valve for controlling flow of an active fluid according to the present disclosure includes a housing, a driven assembly arranged in the housing; and a driving assembly arranged in the housing and configured to drive the driven assembly by magnetic activation such that the driven assembly compresses or decompresses a reservoir. The reservoir is configured to receive active fluid. One of the driven assembly and the housing includes a keyway and the other of the driven assembly and the housing includes a feature that corresponds with the keyway.

DESCRIPTION OF THE FIGURES

The various features and advantages of the disclosed examples will become apparent to those skilled in the art from the detailed description. The figures that accompany the detailed description can be briefly described as follows.

DETAILED DESCRIPTION

Figure 1:
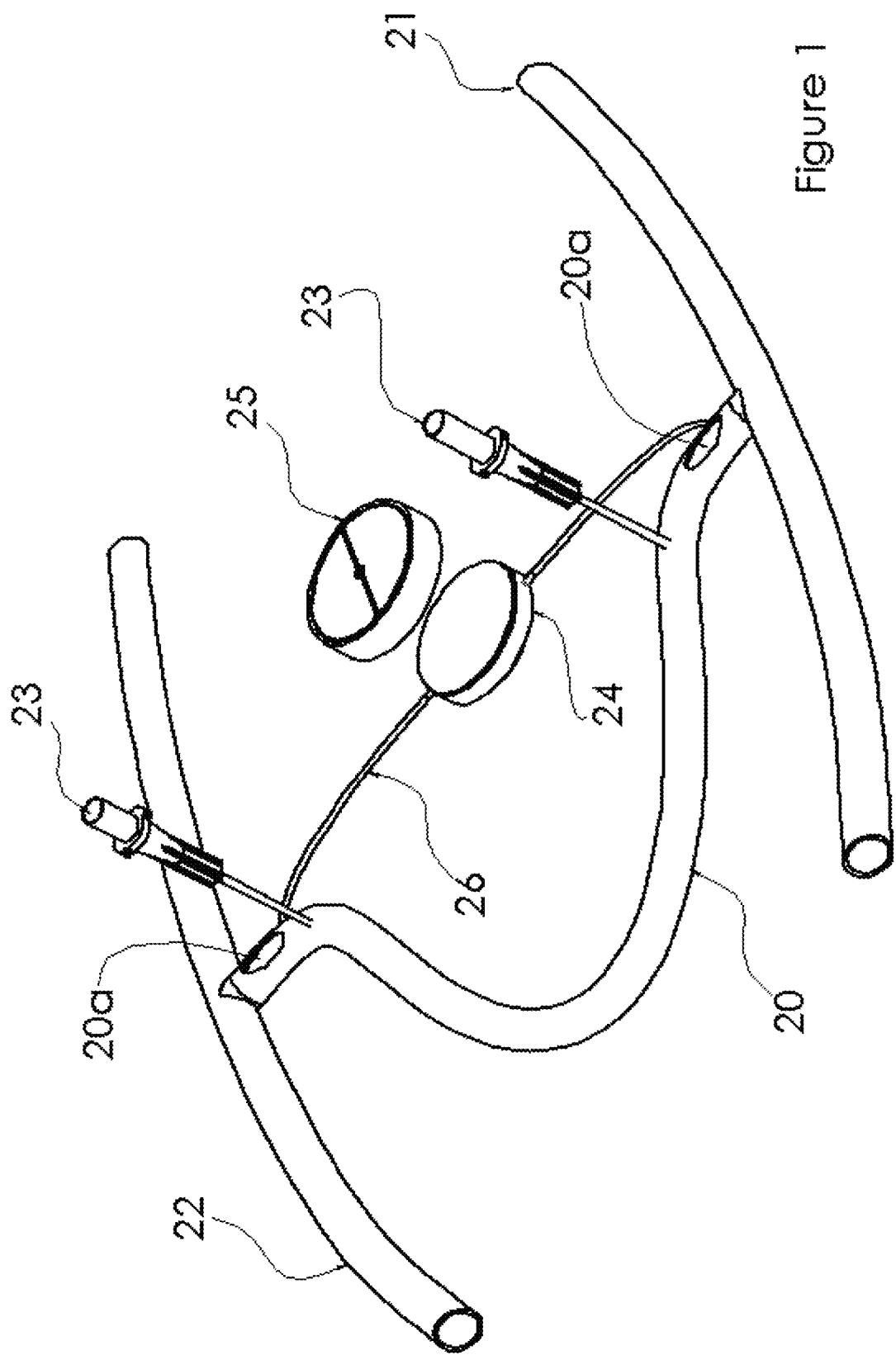
FIG. 1 schematically illustrates an arteriovenous graft.

Medical devices that are implanted in a patient's body can require actuation. One example is an arteriouvenous (AV) graft 20, shown in FIG. 1, which is a biocompatible tube that links a patient's artery 21 and vein 22. The AV graft 20 provides vascular access for hemodialysis. The AV graft 20 has access points 23 for access from outside of the patient's body, to connect to a hemodialysis machine. The AV graft 20 has a valve for controlling blood flow through the graft, such as a balloon valve 20a. The balloon valve 20a in an inflated state blocks blood flow through the AV graft, and in a deflated state allows blood to flow through the AV graft 20. The AV graft 20 also has access points to an active fluid line 26, which includes a valve 24 (e.g., a driven element). An actuator 25 (e.g., a driving element) actuates the valve externally (from outside the body). The active fluid line 26 receives active fluid, such as saline solution. The valve 24 selectively controls the flow of active fluid, which in turn controls blood flow through the AV graft 20. That is, the valve 24 can allow blood flow through the AV graft 20 during the hemodialysis procedure, and disallow blood flow at all other times via the actuator 25. In this way, blood flow between the artery 21 and vein 22 is only allowed when necessary to facilitate hemodialysis, reducing the risk of complications from the unnatural diversion of blood. Though a valve for an AV graft is contemplated, it should be understood that the present disclosure is not limited to AV grafts and can be used in other applications as well.

Turning now to FIGS. 2-5, an example valve 24 and actuator 25 is shown. The example valve 24 in FIGS. 2-5 includes a magnetic coupling, by which it is activated in a contactless manner. That is, the valve 24 can be implanted in a patient's body and the actuator 25 can actuate the valve from outside of the patient's body. In general, magnetic activation is facilitated by providing a set of magnets on a driven element (e.g., the valve 24), the set having an even number of magnets, and a corresponding set of magnets on a driving element (e.g., the actuator 25), the corresponding set having the same even number of magnets as in the driven element. The magnetic activation, defined and characterized by the magnets arrangement and design (geometric shape), can be passive linear, passive nonlinear, hybrid linear, or hybrid nonlinear. "Hybrid" means that valve 24 magnets are all passive magnets and actuator 25 magnets are all active magnets. "Nonlinear" means magnets in the valve 24 have a different geometry (and this produce a different magnetic field) than magnets in the actuator 25. "Linear" means magnets in the valve 24 and actuator 25 have the same geometry.

Figure 2A:
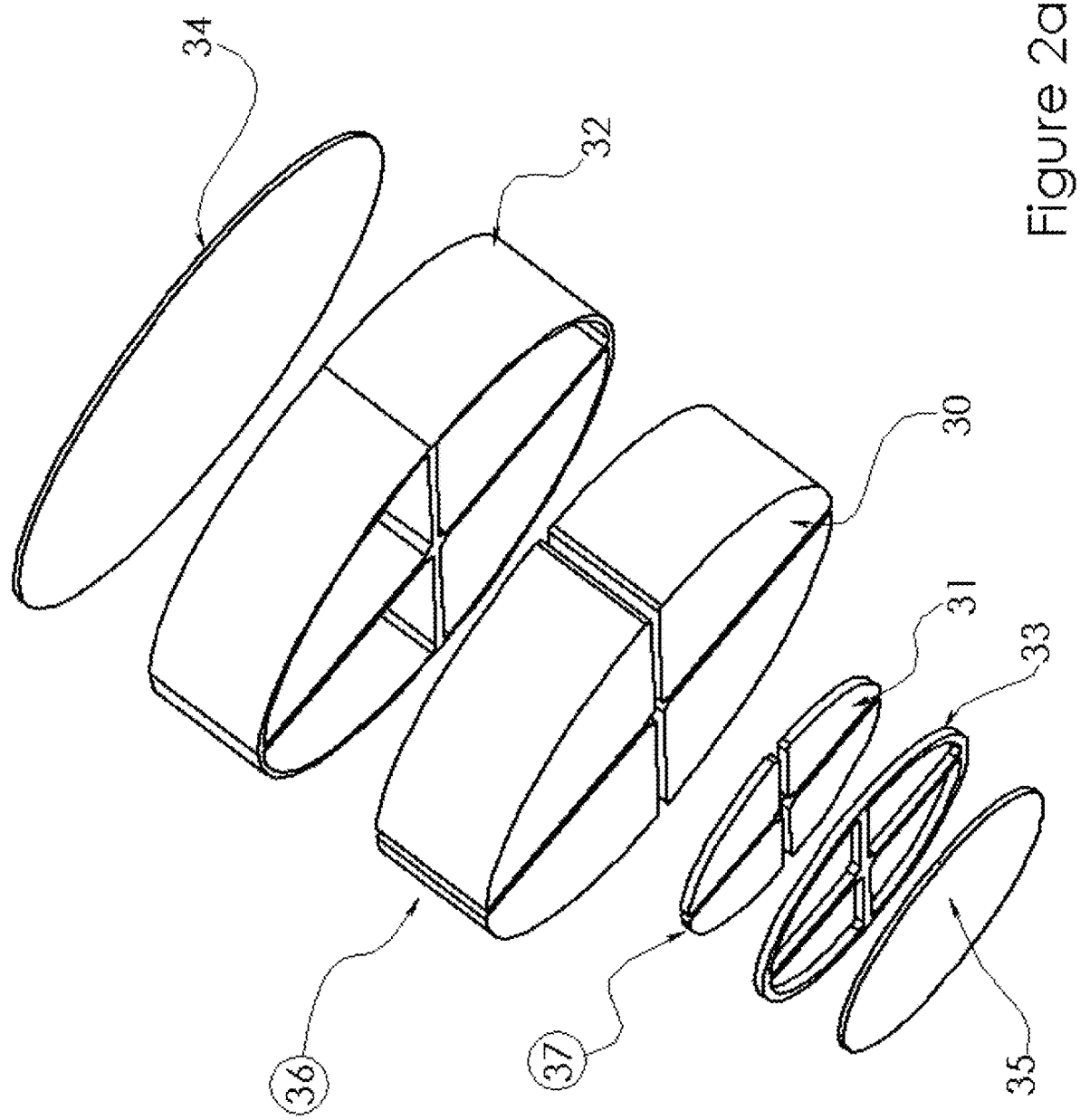
FIG. 2a schematically illustrates an exploded view of a valve with a passive nonlinear magnetic activation scheme.

Referring to FIG. 2A, an exploded view of the example valve 24 and actuator 25 are shown. FIG. 2 illustrates a passive nonlinear magnetic activation scheme. The actuator 25 includes passive magnets 30 arranged in a magnetic core 36. In the example of FIG. 2a, the magnetic core 36 includes four passive magnets 30, however, in another example, any other even number of passive magnets 30 could be used. The magnetic core 36 is arranged in a nonmagnetic insulator 32 which is covered by a soft magnetic alloy disc 34 at one end.

In order to provide magnetic activation, the passive magnets 30 are arranged such that their magnetic field polarities are sequentially in an opposite direction from one magnet 30 to an adjacent magnet 30 in both axial and radial directions. This arrangement allows the passive magnets 30 in the valve 24 to interact with the passive magnets 31 in the actuator 25 (discussed below) and provide magnetic activation of the valve 24.

The valve 24 includes a magnetic core 37 with passive magnets 31 corresponding to the magnetic core 36 in the actuator 25. That is, the magnetic core 37 in valve 24 has the same number of passive magnets 30 as are in the magnetic core 36. As in the actuator 25, the passive magnets 31 are arranged such that their magnetic field polarities are sequentially in an opposite direction from one magnet 31 to an adjacent magnet 31 in both axial and radial directions. This arrangement allows the passive magnets 31 in the actuator 25 to interact with the passive magnets 30 in the valve 24 (discussed above) and provide magnetic activation of the valve 24.

The interaction of the magnets 31 in the valve 24 and the magnets 30 in the actuator 25 due to the magnetic fields oriented as discussed above provides a rotational force and torque on the magnets 30 in the valve 24, which is sufficient to opens and closes the valve 24 (as will be discussed in more detail below).

Figure 2B:
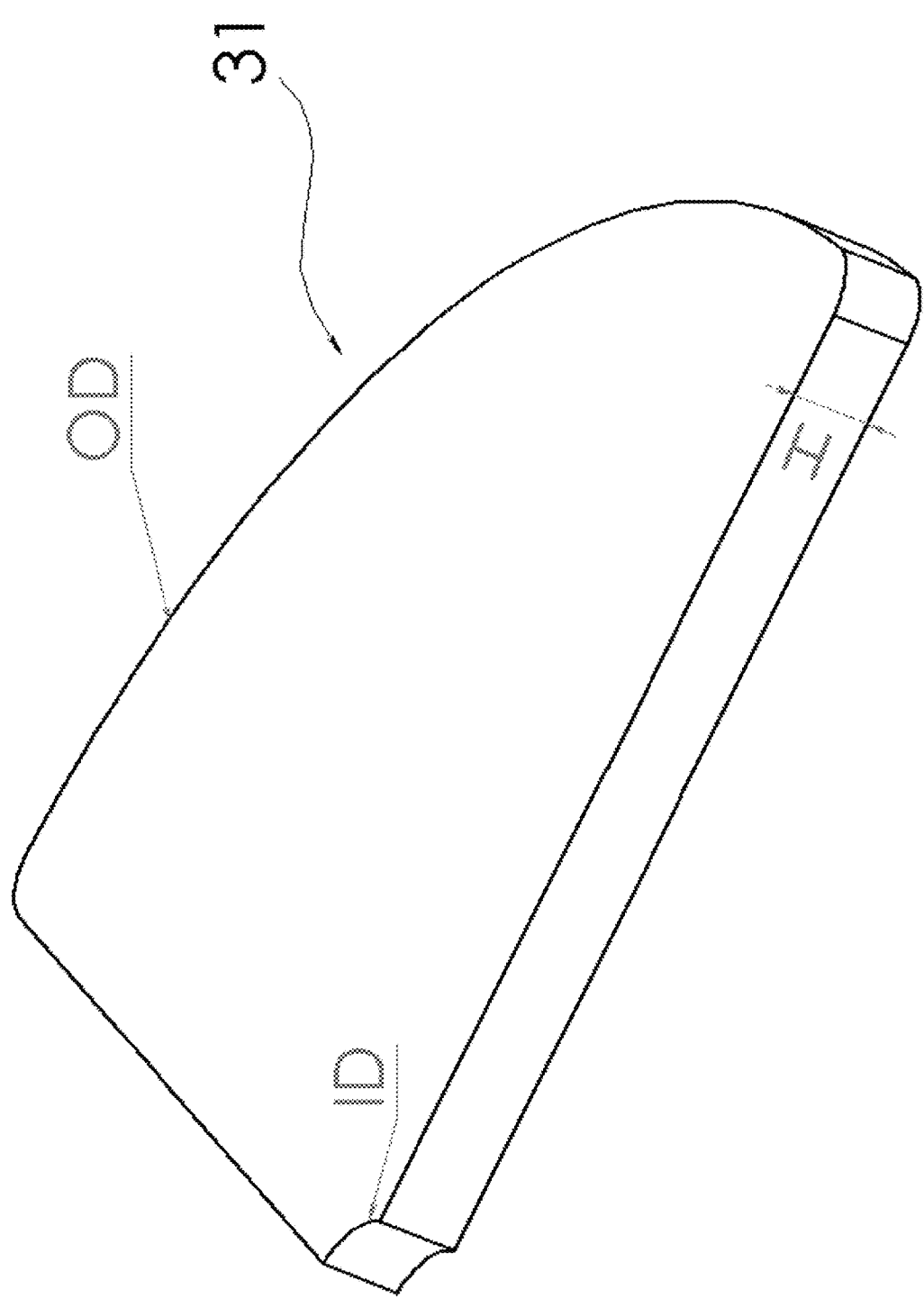
FIG. 2b schematically illustrates a magnet.

The magnets 30, 31 generally have an arcuate shape (shown in FIG. 2b) with an internal diameter (ID), an external diameter (OD) and a height ($H_1$). The arcuate shape maximizes the performance of the magnets 30, 31 by optimizing the active area of the magnetic activation. In the example of FIG. 2a, the magnets 31 in the valve 24 have a lower height H than the magnets 30 in the actuator 25. Accordingly, the example of FIG. 2 depicts a nonlinear activation scheme. The relatively thinner magnets 31 in the valve 24 allow the entire valve 24 implant to be smaller, which is more comfortable for the patient, and easier to implant. The magnets 30, 31 are made of the highest magnetic grade and uniquely designed to minimize the size of the assembly 24, 25 for optimal performance and comfort. In one example, the magnets 30, 31 have a Maximum Magnetic Energy (BH)max of about 56 MGOe (446 KJ/m3) and a Coercive Force (bHc) of about 14.5 kOe (1.154 MA/m).

The soft magnetic alloy discs 34, 35 are located at the backside of the magnet cores 36, 37 active surface, to shield and hold the magnets 30, 31, as well as amplify or enhance the magnetic fields of the magnets 30, 31. The shielding allows for, in one example, shielding of the magnetic field in the implanted valve 24 from imaging techniques such as magnetic resonance imaging (MRI) to reduce or eliminate the effect of the implanted valve 24 on the resulting images.

The saturation thickness $H_{sma}$ of the soft magnetic alloy disks can be estimated using the following correlation:

$$H_{sma} \geq C^{te} \frac{M}{B_{max}} \sum_{i,j} \frac{(D_o^2 - D_i^2)}{(ij\pi)^2 N_P} \frac{\sinh(k(\Delta h)) + \sinh(kh_m)}{\sinh(kh_g)}$$

In general, the design of the magnets is developed by custom-made magnetic finite element software assisted by at least one industrial/commercial electromagnetic FEA (finite element analysis) software for validation. The custom-made FEA output torque/force is a function of several independent variables depicted by the following function:

$$T(a_g, P_g, r_i, r_o, \omega, \Theta, h_i, h_o, h_{si}, h_{so})$$

Figure 13:
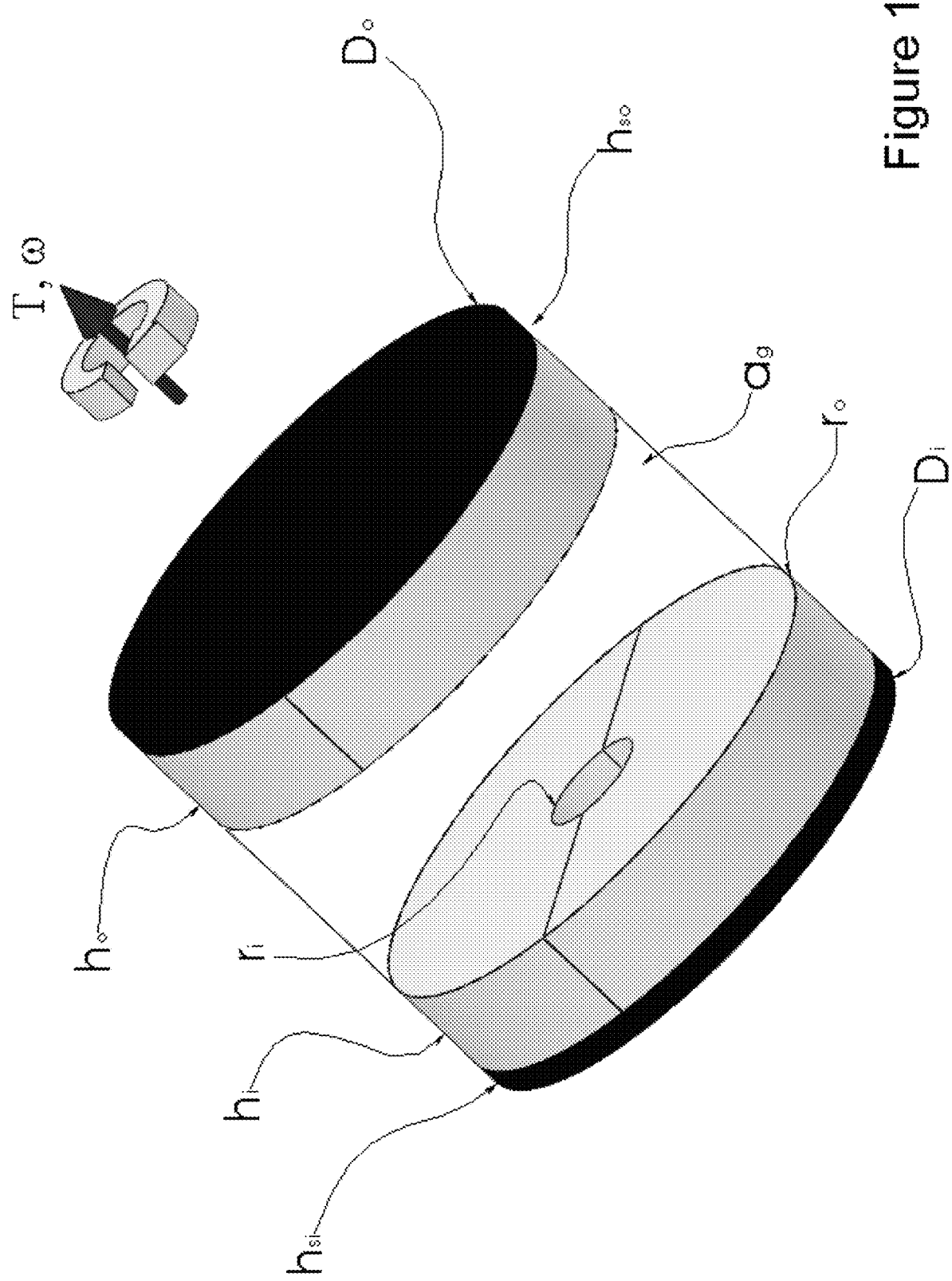
FIG. 13 schematically illustrates a valve showing component dimensions.

Both T and $H_{sma}$ (described above) depend on the following variables, with dimensions shown in FIG. 13.

T: torque
$a_g$: air gap
Pg: magnets poles gap
$r_i$: driven module active/passive magnets radius
$r_o$: driving module active/passive magnets radius
ω: module rotational speed
Φ: poles (pair of active/passive magnets) number
$h_i$: driven module active/passive magnets height
$h_o$: driving module active/passive magnets height
$h_{si}$: driven module soft magnetic disk thickness
$h_{so}$: driving module soft magnetic disk thickness
$C^{te}$: Constant
M: magnetization
$D_{o,i}$: magnets inner and outer diameter
$N_p$: number of poles magnets pairs
k: complex function of diameters and number of pairs f ($D_o$, $D_i$, $N_p$)
$h_{m,g}$: heights (gap, magnets . . . )
Δh: Difference of heights
i,j: integration step size
$B_{max}$: Saturation Magnetization of the Soft magnetic Alloy In one example, the soft magnetic alloy discs 34, 35 properties can have a saturation magnetization of greater than or equal to about 2.4 Tesla.

In one example, the magnets 30, 31 and the soft magnetic alloy discs 34, 35 are coated/plated (e.g., gold-plated) to avoid and/or inhibit any oxidation, corrosion, and/or decay.

Figure 3:
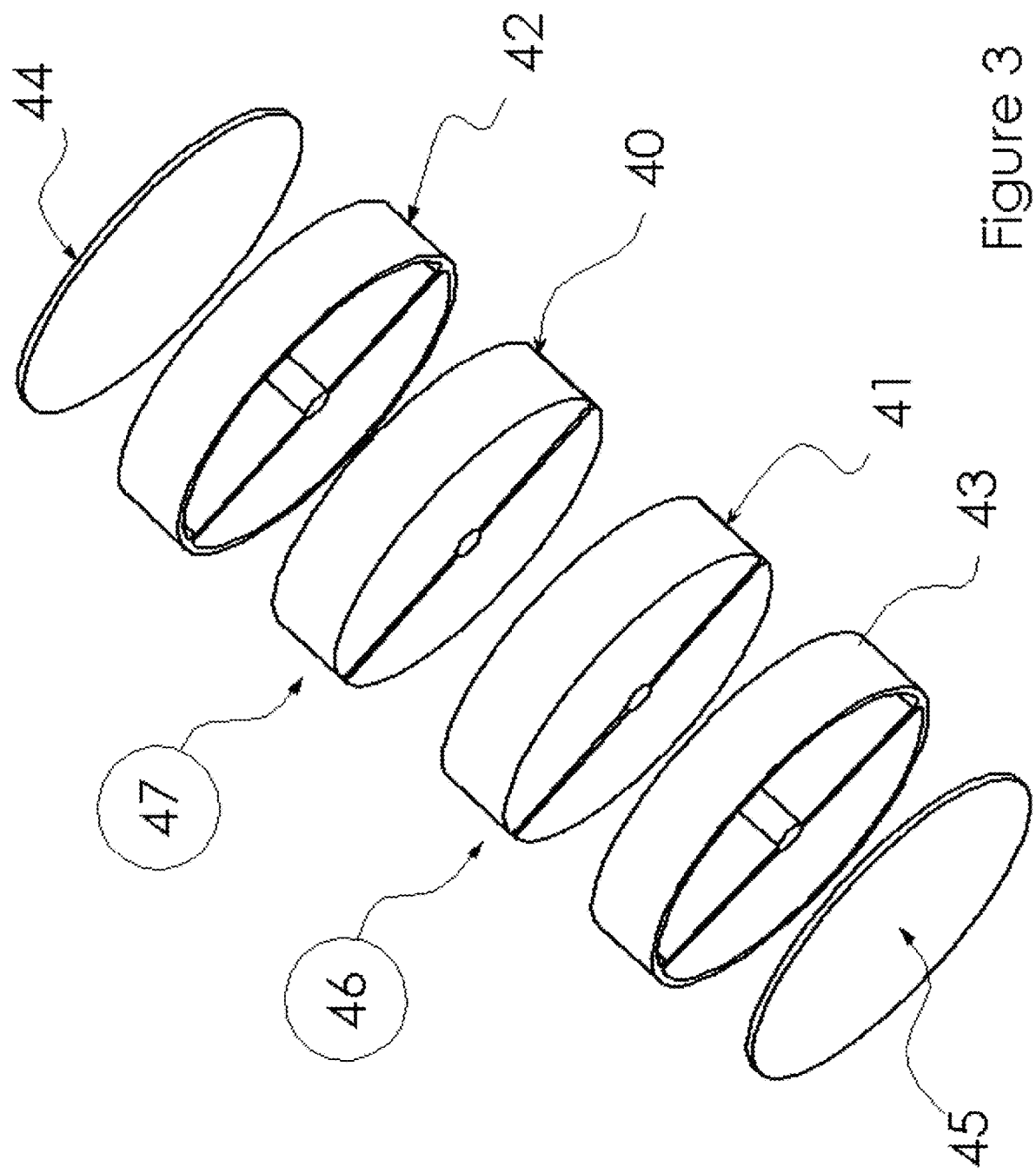
FIG. 3 schematically illustrates an exploded view of a valve with a passive linear magnetic activation scheme.

FIG. 3 illustrates an exploded view of another example valve 24 and actuator 25. FIG. 3 illustrates a passive linear magnetic activation scheme. In the Example of FIG. 3, the valve 24 includes a magnetic core 46 with two passive magnets 41, however, in another example, any other even number of passive nonlinear magnets 41 could be used. The magnetic core 46 is arranged in a nonmagnetic insulator 43 which is covered by a soft magnetic alloy disc 45 at one end. The actuator 25 similarly has a magnetic core 47 with two passive magnets 40 corresponding to the magnetic core 46 of the valve 24 arranged in a nonmagnetic insulator 42 and covered by a soft magnetic alloy disc 44 at one end. In this example, the magnets 40, 41 in the valve 24 and actuator 25 have the same geometry. Therefore, this example is a linear activation scheme.

The magnets 40, 41 and soft magnetic alloy discs 44, 45 can have the properties and characteristics as described above with respect to magnets 30, 31 and soft magnetic alloy discs 34, 35 in FIG. 2 as discussed above.

In the schemes of FIGS. 2 and 3, an external drive (such as a motor) rotates the magnets in the actuator 25, which causes rotation of the corresponding magnets in the valve 24 by way of the magnetic couplings discussed above.

Figure 4:
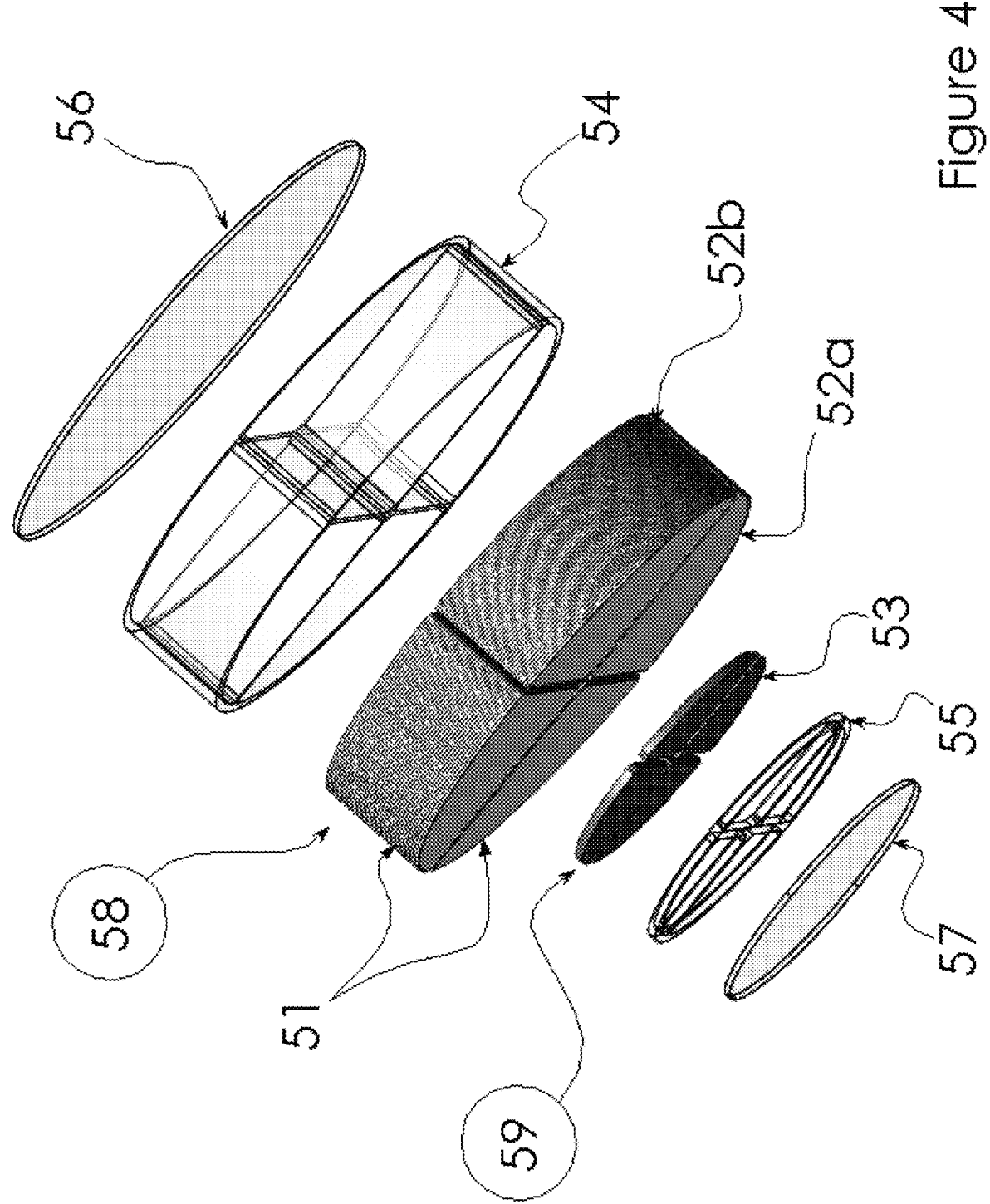
FIG. 4 schematically illustrates an exploded view of a valve with a hybrid nonlinear magnetic activation scheme.

FIG. 4 illustrates an exploded view of another example valve 24 and actuator 25 are shown. FIG. 4 illustrates a hybrid nonlinear magnetic activation scheme. In the example of FIG. 4, the valve 24 includes a magnetic core 59 with four passive magnets 53, however, in another example, any other even number of passive magnets 53 could be used. The magnetic core 59 is arranged in a nonmagnetic insulator 55 which is covered by a soft magnetic alloy disc 57 at one end. The actuator 25 includes a magnetic core 58 with four active magnets 51 corresponding to the four passive magnets 53 in the valve 24. The active magnets 51 are composed of a soft magnetic alloy core 52a and a coil 52b. The coil 52b characteristics (e.g. number of turns, coil inner diameter, etc.) and the electrical current input are selected to provide suitable magnetic activation for system requirements, and depend on the arrangement and geometry of soft magnetic alloy core 52a and passive magnets 53. The magnetic core 58 is arranged in a nonmagnetic insulator 54 and which is covered by a soft magnetic alloy disc 56 at one end. The magnets 51, 53, and soft magnetic alloy discs 56, 57 can have the properties and characteristics as described above with respect to magnets 30 and soft magnetic alloy discs 34, 35 in FIG. 2 as discussed above.

In this example, magnetic activation of magnets 53 in the valve is provided by interaction of the active magnets 51 (e.g., the soft magnetic alloy core 52a interacting with the coil 52b) in the actuator 25 interacting with the passive magnets 53 in the valve 24. Accordingly, this example is a "hybrid" activation scheme.

Like in the example of FIG. 2, in the example of FIG. 4, the passive magnets 53 have a smaller height than the active magnets 53 in the actuator 25. Accordingly, the activation scheme in FIG. 4 is nonlinear.

Figure 5:
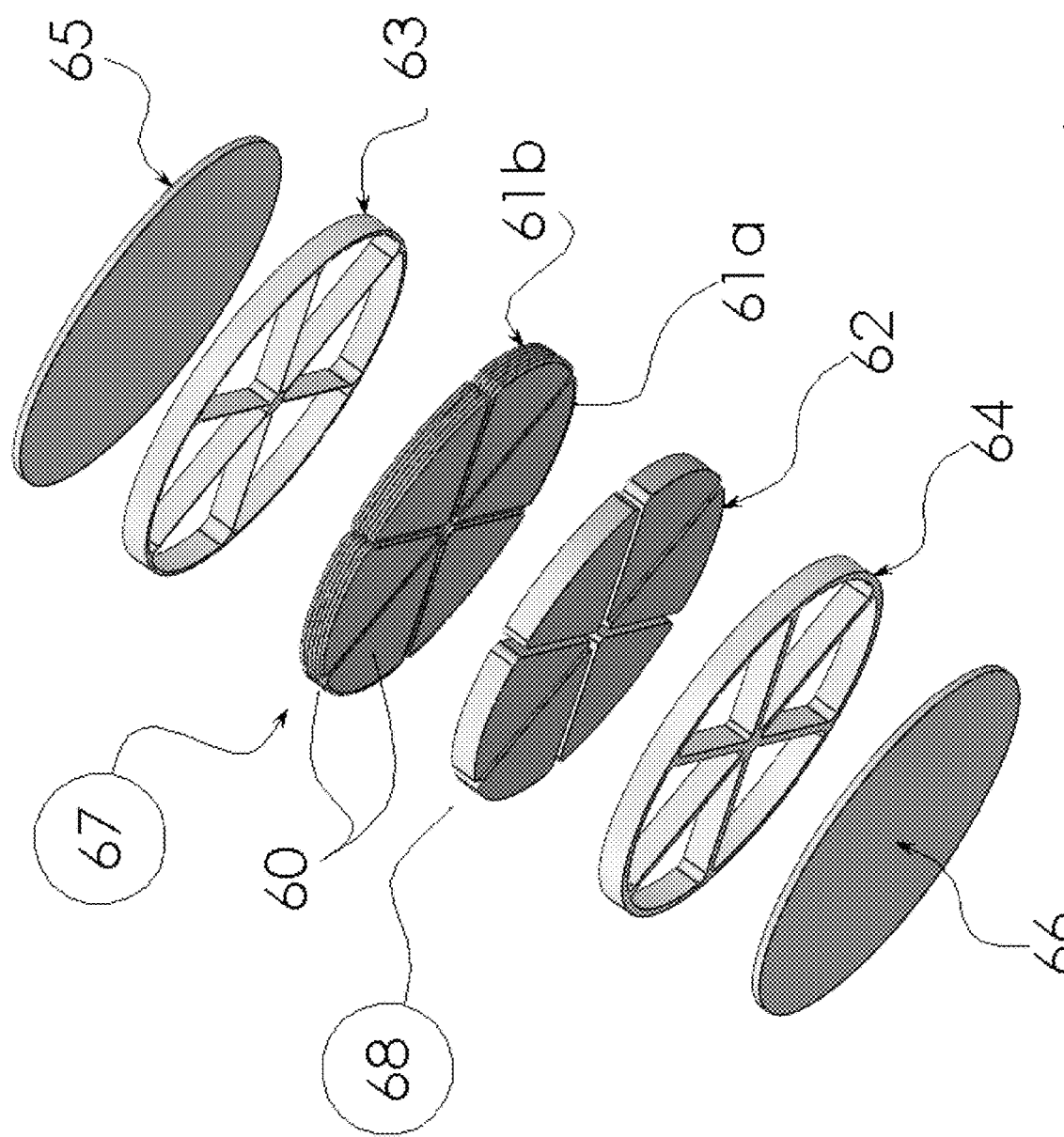
FIG. 5 schematically illustrates an exploded view of a valve with a hybrid linear magnetic activation scheme.

FIG. 5 illustrates an exploded view of another example valve 24 and actuator 25 are shown. FIG. 5 illustrates a hybrid linear magnetic activation scheme. In the example of FIG. 5, the valve 24 includes a magnetic core 68 with six passive magnets 62, however, in another example, any other even number of passive linear magnets 62 could be used. The magnetic core 68 is arranged in a nonmagnetic insulator 64 which is covered by a soft magnetic alloy disc 66 at one end. The actuator 25 includes a magnetic core 67 with six active magnets 60 corresponding to the six passive magnets 62 in the valve 24. The active magnets 60 are composed of a soft magnetic alloy core 61a and surrounded by a coil 61b. The magnetic core 67 is arranged in a nonmagnetic insulator 63 and which is covered by a soft magnetic alloy disc 65 at one end. The magnets 60, 62 and soft magnetic alloy discs 65, 66 can have the properties and characteristics as described above with respect to magnets 30, 31 and soft magnetic alloy discs 34, 35 in FIG. 2 as discussed above.

In the hybrid schemes of FIGS. 4 and 5, a current is provided to the coils in the actuator 25 from an external power source, which induces a magnetic field in the magnets in the actuator 25 and causes movement of magnets in the valve 24 towards and away from the magnets in the actuator 25 by way of the magnetic couplings discussed above.

The table below summarizes example magnet dimensions for the magnets discussed in FIGS. 2-5. $H_1$ is the height of the magnets in the valve 24 or actuator 25, and $H_2$ is the height of the soft magnetic alloy discs 65, 66.

TABLE 1

| Sample Model | Magnets in Actuator 25 | | | | Magnets in Valve 24 | | | |
|---|---|---|---|---|---|---|---|---|
| | ID (mm) | OD (mm) | $H_1$ (mm) | $H_2$ (mm) | ID (mm) | OD (mm) | $H_1$ (mm) | $H_2$ (mm) |
| Passive Nonlinear (FIG. 2) | 2.0 | 34.0 | 10.0 | 1.0 | 2.0 | 28.0 | 0.8 | 0.3 |
| Passive Linear (FIG. 3) | 2.0 | 19.2 | 2.8 | 1.0 | 2.0 | 19.2 | 2.8 | 0.3 |
| Hybrid Nonlinear (FIG. 4) | 2.0 | 22.0 | 5.0 | 0.5 | 2.0 | 22.0 | 0.3 | 0.3 |
| Hybrid Linear (FIG. 5) | 2.0 | 18.0 | 1.6 | 0.3 | 2.0 | 18.0 | 1.6 | 0.3 |

Turning now to FIGS. 6-10, a valve actuation scheme 70 for controlling the flow of active fluid in the active fluid line 26 is disclosed. The valve actuation scheme can be used in the valve 24 above, for example. More generally, the valve actuation scheme 70 includes an implant 71 and an actuator 85. The implant 71 is implanted in the body along the active fluid line 26 while the actuator 85 remains outside of the body.

The implant 71 includes a housing module 72 and an activated/driven assembly 73 inside the housing module 72. The activated/driven assembly 73 is externally driven by the actuator 85 which is supported internally by a passive mechanical support (e.g. spring 81) and/or by a passive thermally responsive support (e.g. balloon 82). The balloons 82 are pressurized with a fluid that is thermally responsive (that is, the pressure in the balloon 82 changes with thermal changes, which in turn changes the amount of force exerted by the balloons 82 on the driven assembly 73. In this example, the actuation of the driven assembly 73 is by translational motion of the driven assembly 73. The housing module 72 includes a container 74, a cover 75, and a reservoir/accumulator 76 in fluid communication with one or more fluid outlets 78, which in turn are in fluid communication with the active fluid line 26. The driven assembly 73 includes a soft magnetic alloy disc 79 (such as one of the soft magnetic alloy discs discussed above) with one or more keys 77, a passive magnet 83, and a separator 74 between the soft magnetic alloy disc 79 and the passive magnet 83.

The keys 77 are received in a keyway 80 in the container 74. The keys 77/keyway 80 maintain the alignment of the soft magnetic alloy disc 79 in the housing module 72 while allowing it to move axially (e.g., translational motion) within the housing module 72. In general, rotational motion can be provided by an external drive (e.g. motor) to the actuator 85 magnets, which causes passive magnets 83 in the implant 71 to rotate due to magnetic coupling. The passive magnet 83 is connected to the soft magnetic alloy disc 79. As the passive magnets 83 and soft magnetic alloy disc 79 move, fluid is forced into and out of the AV graft 20 valve 20a as discussed below.

Figure 6:
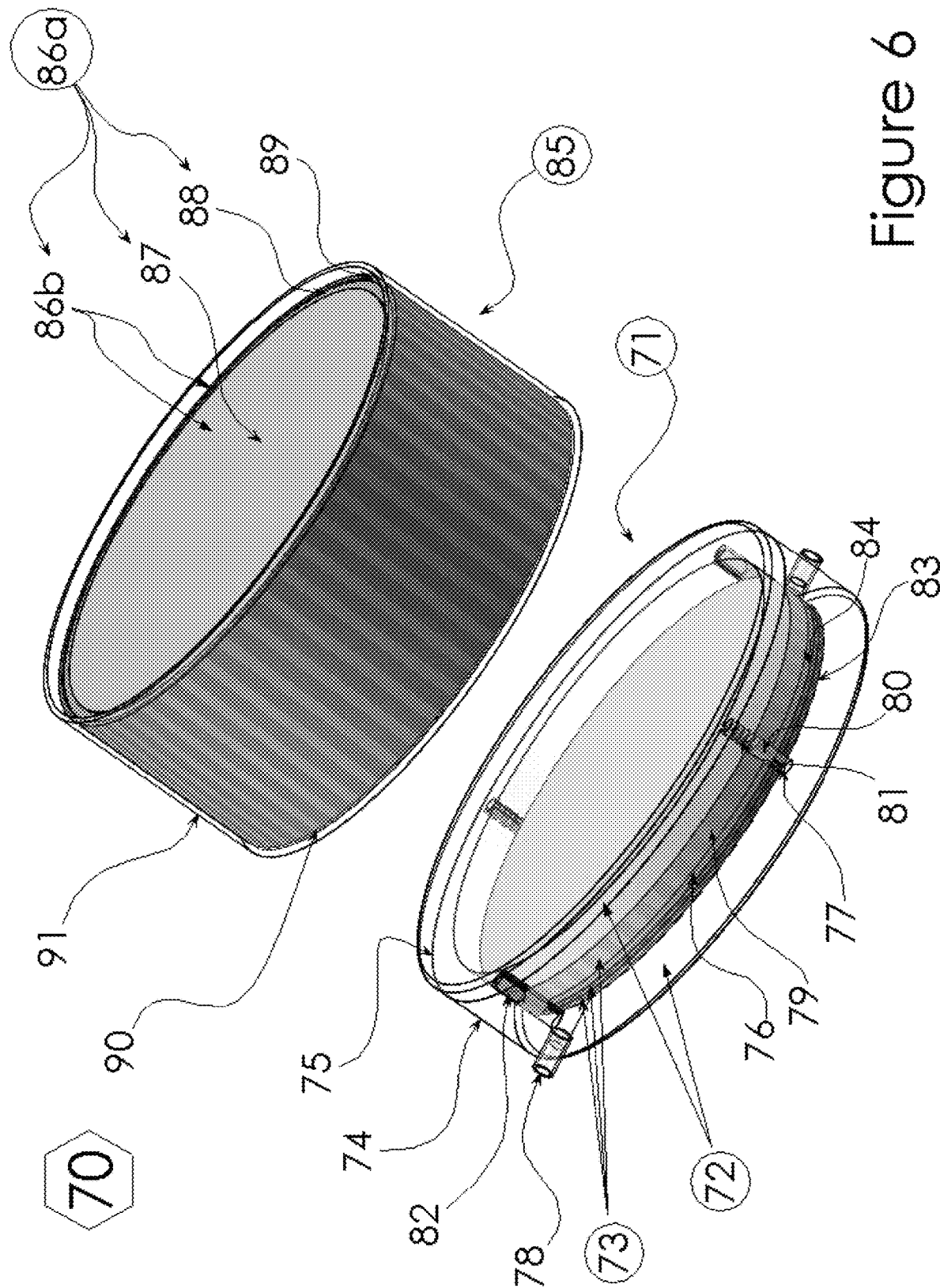
FIG. 6 schematically illustrates an example valve actuation scheme.
Figure 7:
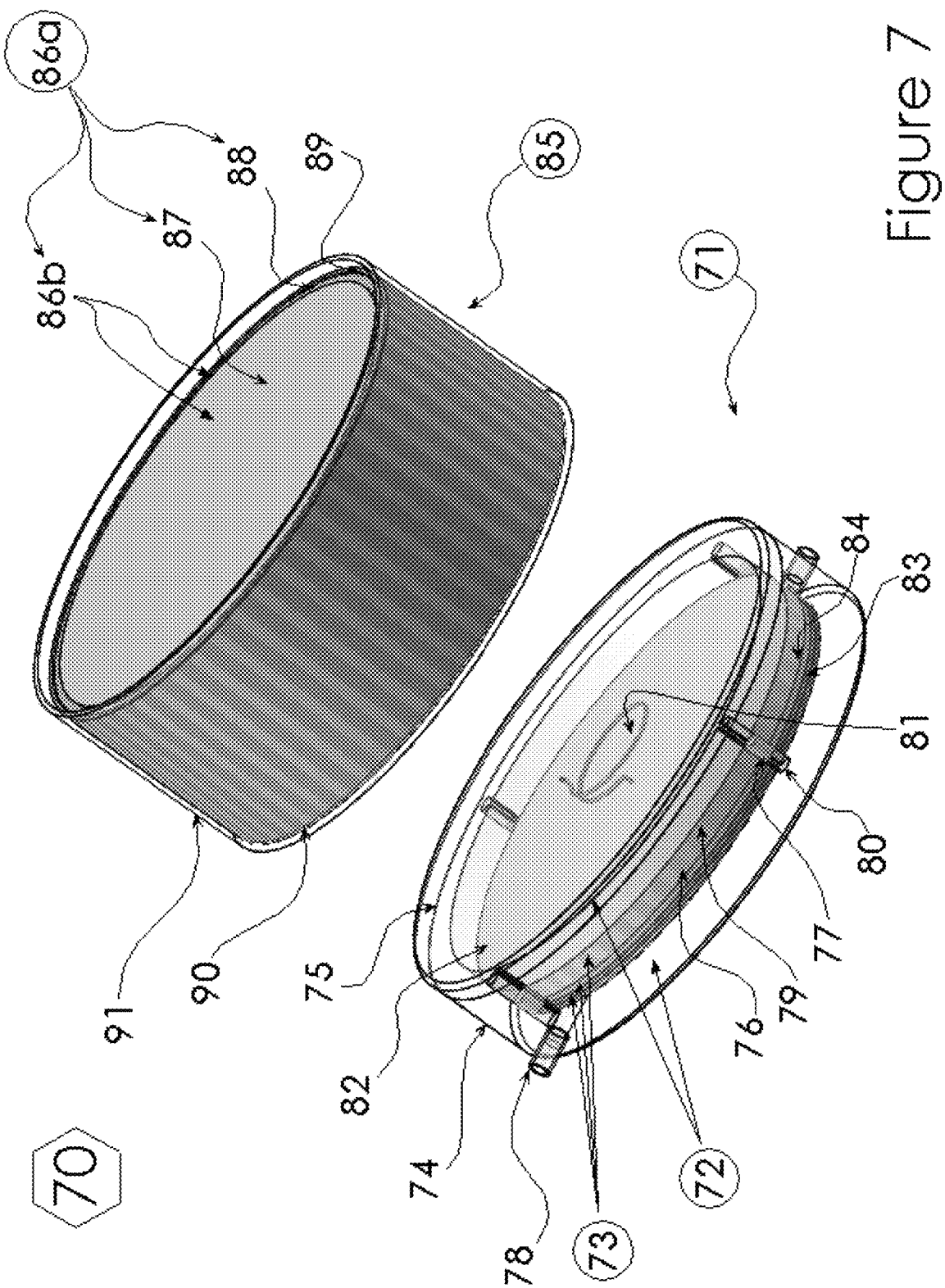
FIG. 7 schematically illustrates an alternate example valve actuation scheme.
Figure 8:
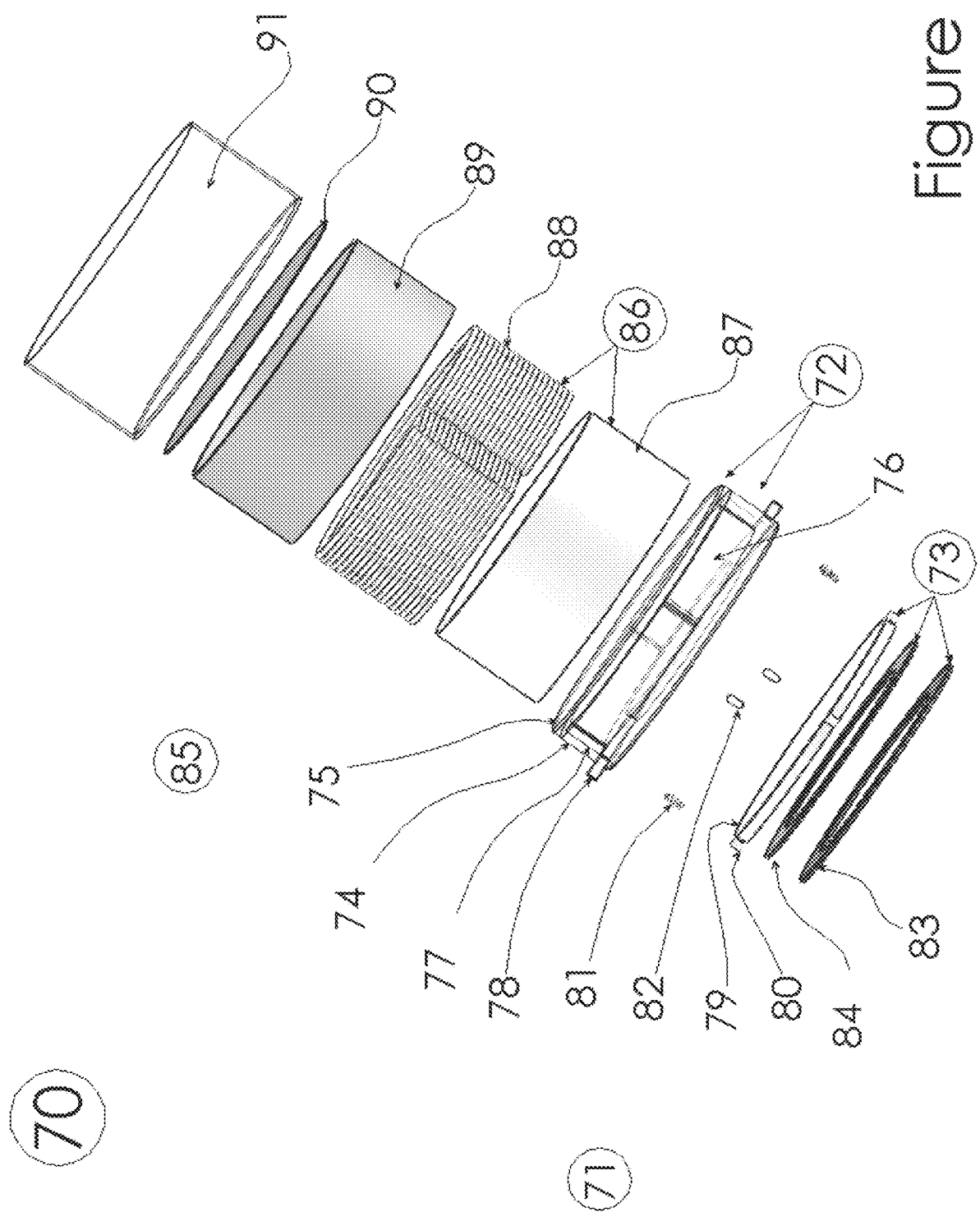
FIG. 8 schematically illustrates an exploded view of the valve actuation scheme of FIG. 6.
Figure 9:
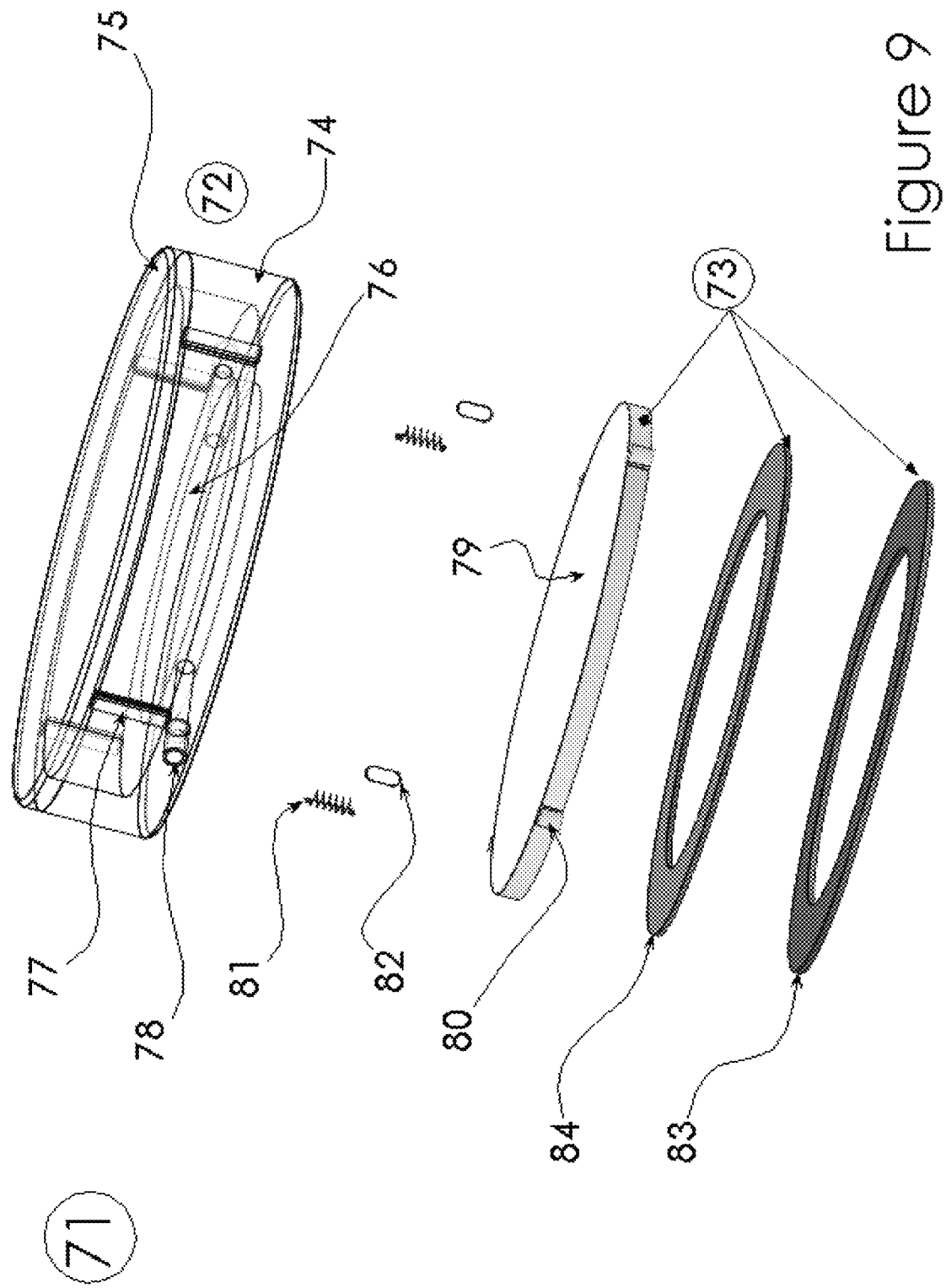
FIG. 9 schematically illustrates an exploded view of a valve in the valve actuation scheme of FIG. 6.
Figure 10:
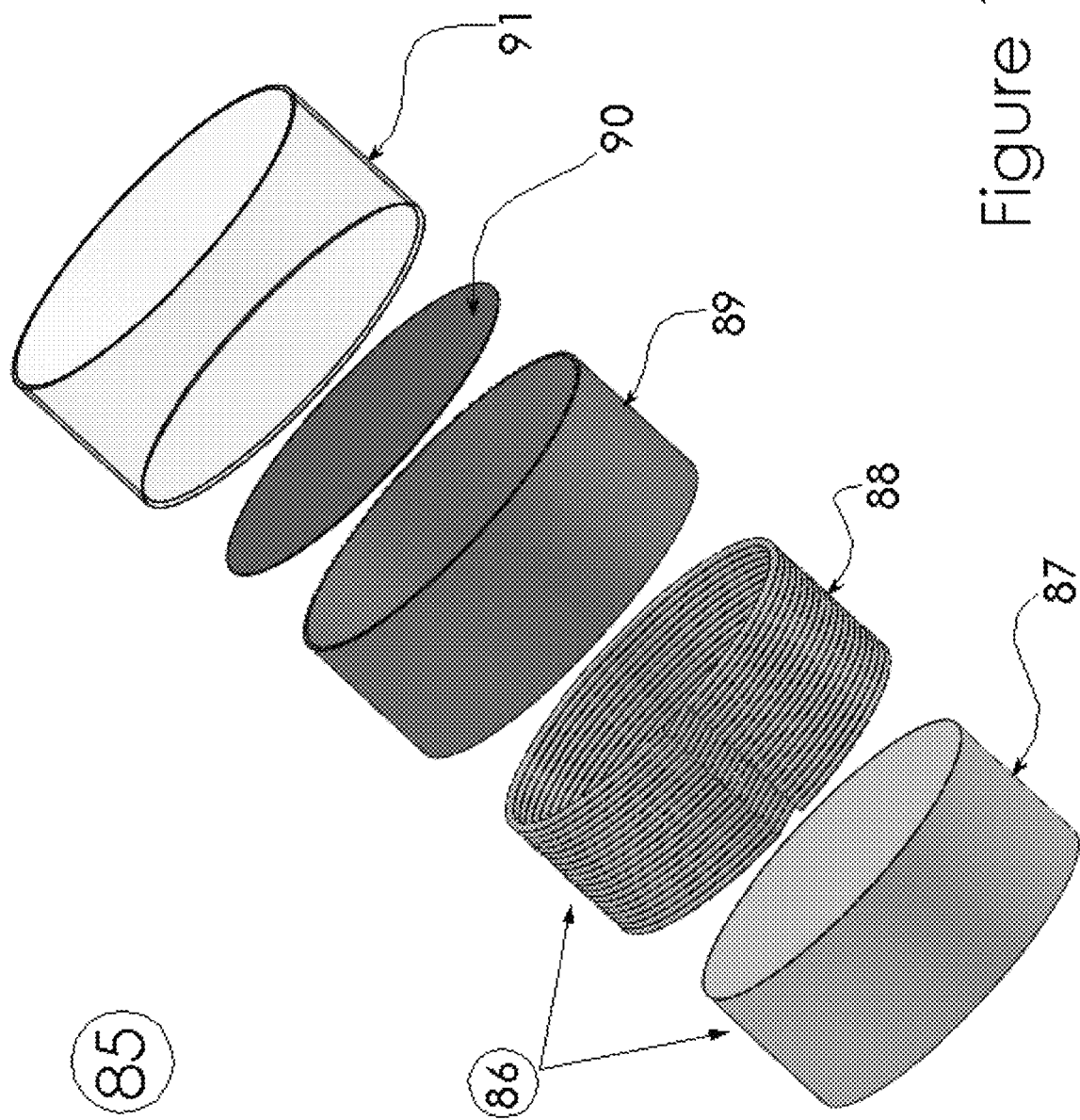
FIG. 10 schematically illustrates an exploded view of an actuator in the valve actuation scheme of FIG. 6.

In one example, a feature such as a spring 81 and/or a balloon 82 is arranged adjacent the keys 77 in the keyway 80 to maintain a position of the soft alloy disc 79 in a resting state, as shown in FIGS. 6 and 8. In other words, the spring 81 and/or the balloons 82 provide passive support for the soft magnetic alloy disc 79. In another example, a spring 81 is between the soft magnetic alloy disc 79 and the container 74, as shown in FIG. 7. The springs 81 are non-magnetic and have high corrosion resistivity and a high frequency life cycle. In the resting state the soft magnetic alloy disk 79 is locked with the passive magnet 83, compressing the reservoir/accumulator 76 and draining the active fluid into the balloon valve 20*a*, which blocks the blood from flowing between artery 21 and vein 22 as discussed above When activated by magnetic activation, as discussed in more detail below, the actuator 85 moves the soft magnetic alloy disk 79 away from the passive magnet 83, decompressing the reservoir/accumulator 76, which drains the balloon valve 20*a* active fluid into the reservoir/accumulator 76 and allows blood to flow between artery 21 and vein 22.

Similar to the hybrid magnetic activation schemes discussed above, in one example, the actuator 85 includes a driving assembly 86*a*, which in turn includes a non-magnetic base 90, a body 91, and an active magnet 86*b*. The active magnet 86*b* includes a soft magnetic alloy core 87 wrapped with a coil 88, and the soft magnetic alloy core 87 and coil 88 are arranged in a non-magnetic shell 89. The number of turns of the coil 88 is selected to provide the required power to activate the magnet 83 in the implant 71, and depends on the particular configuration and geometry of the soft magnetic alloy core 87 and the passive magnet 83.

The active magnet 86*b* in the actuator 85 interacts with the passive magnets 83 in the implant 71 when a current is applied to the coil 88 via an external power source to generate a magnetic field to overcome the resistive forces provided by the springs 81 and/or balloons 82 and move the soft magnetic alloy disc 79 out of the resting state and into the active state, as discussed above.

Figure 11:
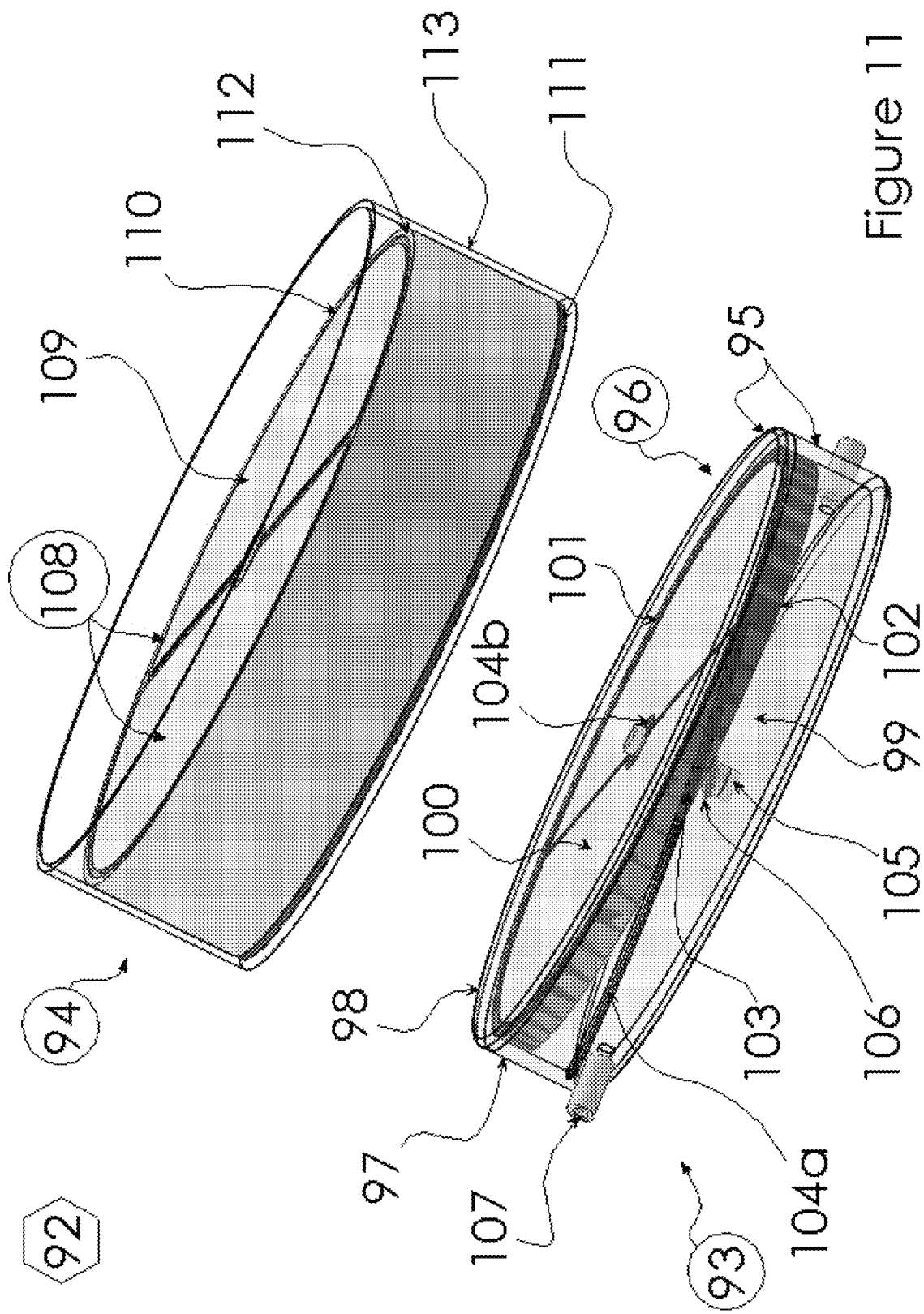
FIG. 11 schematically illustrates an alternate valve actuation scheme.
Figure 12:
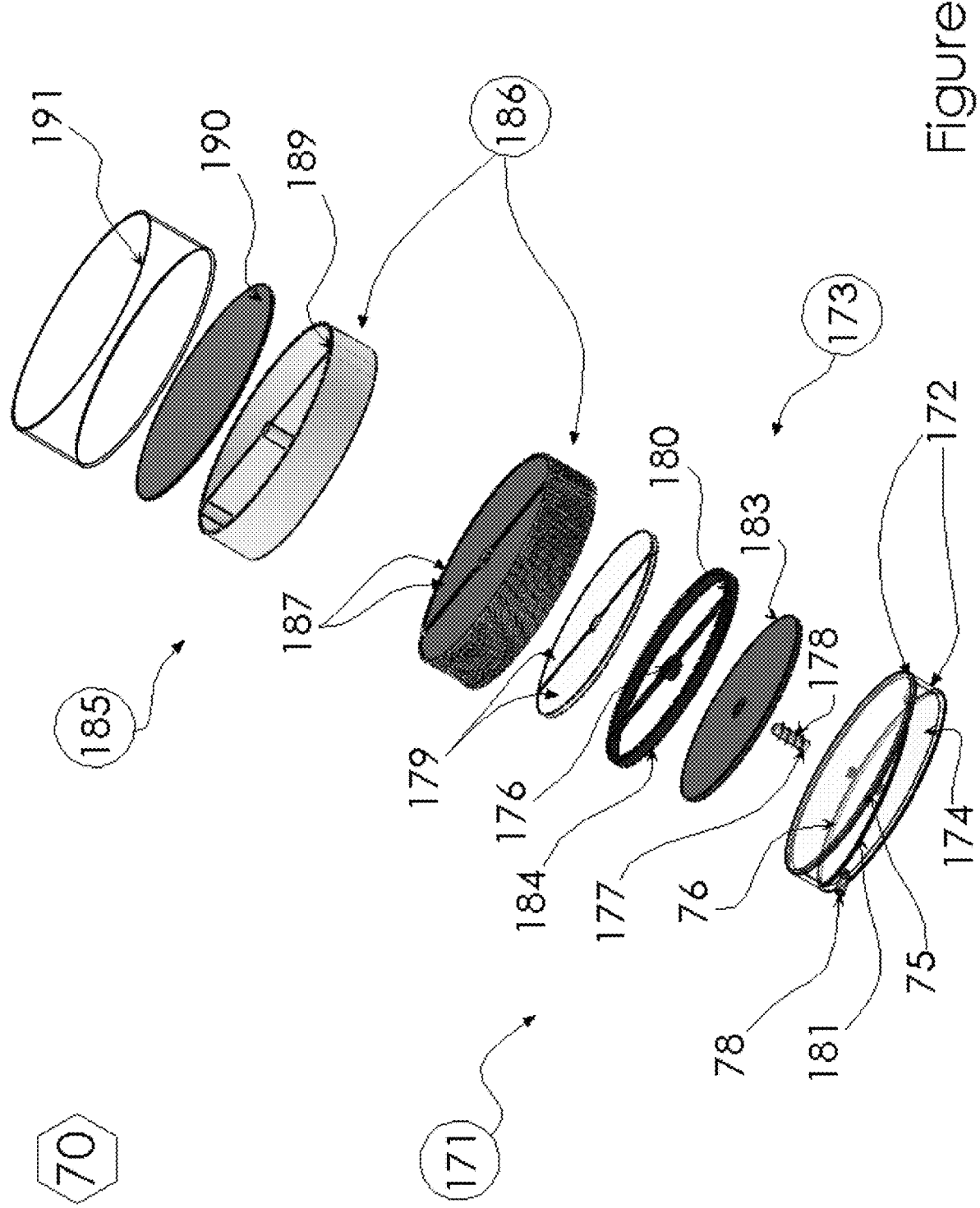
FIG. 12 schematically illustrates an exploded view of the alternate valve actuation scheme of FIG. 11.

Turning now to FIGS. 11-12, an alternate valve actuation scheme with implant 171 and actuator 185 are shown. The alternate implant 171 includes a housing module 172 and an activated/driven assembly 173 inside the housing module 172. The housing module 172 includes a container 174, a cover 75, and a reservoir/accumulator 76 in fluid communication with one or more fluid outlets 78, which in turn are in fluid communication with the active fluid line 26.

The activated/driven assembly 173 is externally driven by the actuator 185. In this example the motion of the activated/driven assembly 173 is rotational. The driven assembly 173 includes passive magnets 179, and a soft magnetic alloy disc 183 attached to a nonmagnetic separator 184. The housing module 172 includes a shaft 177 extending through its center and through a hole in the driven assembly 173. The hole in the driven assembly 173 includes a keyway 178 around its surface. The shaft 177 includes a thread 176 which interacts with the keyway 178. The outer surface of the nonmagnetic separator 184 also includes a keyway 180 that interacts with a thread 181 on the container 174. When the nonmagnetic separator 184 is moved from the resting state as discussed above, it rotates. The keyway 178 and corresponding thread 176 and the keyway 180 corresponding to thread 181 provide a track along which the nonmagnetic separator 184 moves axially within the housing module 172 as it rotates due to magnetic activation, compressing or decompressing the reservoir/accumulator 76 as discussed above.

The actuator 185 includes a driving/activator assembly 186, a housing 191 and a separator 190. The driving assembly 186 includes the same number of passive or active magnets 187 as in the activated/driven assembly 173 and is surrounded by a nonmagnetic shell 189. The implant 171 and actuator 185 include the appropriate components for any of the magnetic activation schemes discussed above and shown in FIGS. 2-5.

The preceding description is exemplary rather than limiting in nature. Variations and modifications to the disclosed examples may become apparent to those skilled in the art that do not necessarily depart from the essence of this disclosure. Thus, the scope of legal protection given to this disclosure can only be determined by studying the following claims.

I claim:

1. A magnetically activated implantable valve, comprising:
an implantable valve, the implantable valve including a first set of passive magnets; and
an actuator configured to actuate the implantable valve, the actuator including a second set of passive magnets corresponding to the first set of passive magnets, wherein the first set of passive magnets is configured to interact with the second set of passive magnets to actuate the valve, wherein the first and second sets of magnets each have an even number of magnets, wherein each of the implantable valve and the actuator further include a soft magnetic alloy disc configured to shield and support the first and second sets of magnets, respectively.

2. The magnetically activated implantable valve of claim 1, wherein the passive magnets in the first and second sets of magnets each have an arcuate shape with a height.

3. The magnetically activated implantable valve of claim 2, wherein passive magnets in the first set of passive magnets have the same geometry than passive magnets in the second set of passive magnets.

4. The magnetically activated implantable valve of claim 1, wherein the passive magnets in each of the first and second sets of magnets are arranged such that their magnetic field polarities are sequentially in an opposite direction from a first passive magnet to a second passive magnet adjacent the first passive magnet in both axial and radial directions.

5. The magnetically activated implantable valve of claim 1, wherein the implantable valve is arranged on an active fluid line of an arteriovenous graft, and is configured to control blood flow through the arteriovenous graft.

6. An implantable valve for controlling flow of an active fluid, comprising:
a housing;
a driven assembly arranged in the housing; and
a driving assembly arranged in the housing and configured to drive the driven assembly by magnetic activation such that the driven assembly compresses or decompresses a reservoir, the reservoir configured to receive active fluid, wherein one of the driven assembly and the housing includes a keyway and the other of the driven assembly and the housing includes a feature that corresponds with the keyway.

7. The implantable valve of claim 6, wherein the driving assembly drives the driven assembly in a translational motion.

8. The implantable valve of claim 7, wherein the housing includes the keyway, and the driven assembly includes keys that correspond to the keyway.

9. The implantable valve of claim 7, further comprising a feature configured to maintain the driven assembly in a resting state.

10. The implantable valve of claim 6, wherein the driving assembly drives the driven assembly in a rotational motion.

11. The implantable valve of claim 9, wherein the driven assembly includes a hole with a keyway on the surface of the hole, and the housing includes a shaft with a thread that corresponds to the keyway.

12. The implantable valve of claim 9, wherein the driven assembly includes a keyway on an outer surface, and the housing includes a thread that corresponds to the keyway.

\* \* \* \* \*